United States Patent [19]

Wildi et al.

[11] B 4,013,514

[45] Mar. 22, 1977

[54] PREPARING A REACTOR CONTAINING ENZYMES ATTACHED TO DIALDEHYDE CELLULOSE

[75] Inventors: Bernard S. Wildi, Kirkwood; Lloyd E. Weeks, Creve Coeur, both of Mo.

[73] Assignee: Monsanto Company, St. Louis, Mo.

[22] Filed: Jan. 2, 1974

[21] Appl. No.: 430,213

[44] Published under the second Trial Voluntary Protest Program on March 30, 1976 as document No. B 430,213.

Related U.S. Application Data

[63] Continuation-in-part of Ser. No. 215,432, Jan. 4, 1972, abandoned.

[52] U.S. Cl. .............................. 195/68; 195/31 R; 195/63; 195/DIG. 11; 426/12
[51] Int. Cl.² ........................................ C07G 7/02
[58] Field of Search .............. 195/63, 68, DIG. 11, 195/31 R; 426/12

[56] References Cited

UNITED STATES PATENTS

| | | | |
|---|---|---|---|
| 3,705,084 | 12/1972 | Reynolds | 195/63 |
| 3,706,633 | 12/1972 | Katchalski et al. | 195/63 |
| 3,753,861 | 8/1973 | Forgione | 195/68 |

FOREIGN PATENTS OR APPLICATIONS 83,154   7/1971   Germany

OTHER PUBLICATIONS

Weliky et al., The Chemistry and Use of Cellulose Derivatives for the Study of Biological Systems, Immunochemistry, Vol. 2, 1965, (pp. 293-305).

*Primary Examiner*—David M. Naff
*Attorney, Agent, or Firm*—Gordon W. Hueschen; John D. Upham; Joseph D. Kennedy

[57] ABSTRACT

Water-insoluble, biologically active conjugates for use in a reactor core of a flow-through reactor are prepared by covalently bonding an enzyme directly to a fibrous dialdehyde cellulose such as cotton. Preferably the fibrous cellulose is placed in the reactor core of a flow-through reactor before or after it is treated with periodic acid solution to convert glucose units thereof to units containing dialdehyde groups. Thereafter, an enzyme solution is passed through the resultant dialdehyde cellulose to bind the enzyme to the cellulose.

8 Claims, No Drawings

PREPARING A REACTOR CONTAINING ENZYMES ATTACHED TO DIALDEHYDE CELLULOSE

CROSS REFERENCE TO RELATED APPLICATION

This application is a continuation-in-part of our prior application, Ser. No. 215,432, filed Jan. 4, 1972, now abandoned.

BACKGROUND OF THE INVENTION

This invention relates to water-insoluble derivatives of biologically-active enzymes.

The utility of enzymes as catalysts is well established.

Immobilized derivatives of active enzymes are useful as readily removable catalysts for various biochemical reactions such as proteolysis, curdling of milk, conversion of starch to glucose, conversion of glucose to fructose, hydrolysis of pectins, and the like.

It is known to prepare such immobilized protein derivatives by attaching a biologically-active protein such as an enzyme to a carrier which is insoluble in aqueous solutions or which becomes insoluble as a result of the protein attachment. The attachment is made through a functional group of the protein which is not essential for biological activity. In such a manner a biologically-active yet water-insoluble conjugate can be produced. It is known to produce such conjugates by several distinct methods such as adsorption, ion-exchange, formation of a covalent bond between the protein and the carrier, crosslinking, inclusion, and polymerization.

The present invention falls into the general category where a covalent bond is formed between the enzyme and the water-insoluble carrier. Enzymes insolubilized on an inert matrix by covalent bonding can be used as a reactor core for efficient continuous conversion processes of various substrates. By passing a suitable substrate solution through such an enzyme reactor large quantities of the substrate can be exposed to a fixed quantity of the enzyme and thus converted into desired products. The enzymatically active reactor core can be used for long time periods, and there exists no need for a subsequent separation of the enzyme catalyst from the substrate because the enzyme is retained within the reactor and the conversion reaction is automatically stopped when the substrate solution, together with the reaction products, exits from the reactor.

In preparing immobilized enzyme conjugates it is important that the methods utilized to effect covalent bonding of the enzyme to the carrier or matrix do not inactivate the enzyme and do not destroy the structural integrity of the matrix. Enzymes are usually quite unstable and cannot be subjected to severe reaction conditions without adversely affecting activity. As to the carrier or matrix, in a flow-through reactor the liquid permeability of the reactor core is very important from a practical process standpoint and any damage to or weakening of the intended matrix should be avoided.

While it is known to insolubilize proteins such as enzymes by covalent bonding to an inert matrix or carrier, the preparation of a matrix which is reactive toward the enzyme yet suitable for use as a flow-through reactor core is often complicated, laborious, and expensive.

Goldstein et al., Biochemistry 9, No. 11, 2322-2333 (1970), disclose a matrix which is dialdehyde starch crosslinked with a bifunctional reactant such as methylene dianiline in order to render the matrix water-insoluble and in order to provide, by means of bifunctional reagent molecules attached to the crosslinked starch at one point only, reactive sites for coupling to an enzyme. The enzyme is not attached directly to the dialdehyde starch but to the free functional group of the bifunctional reactant by diazotization. While a good, enzymatically-active product, representing an improvement over enzymes attached by diazotization to p-aminobenzyl cellulose (Goldstein et al., p. 2331) can be produced in such a manner, it is readily apparent to one skilled in the art that the preparation of such a product is still involved and expensive.

It is an object of the present invention to provide a biologically-active, water-insoluble dialdehyde celluloseenzyme conjugate having relatively high biological activity yet which can be readily and inexpensively produced.

It is a further object to provide a high-activity flow-through reactor having a water-insoluble dialdehyde cellulose core with a biologically-active enzyme covalently bonded directly to the core.

It is another object of this invention to provide a method for producing a biologically-active, flow-through reactor.

It is a more specific object of this invention to provide a method for making a liquid permeable cellulose/enzyme conjugate in place, ready for use for treating various liquids which can be passed through the reactor without the necessity for further handling of the cellulose/enzyme product to ready it for use.

It is an additional object to provide a method for firmly and directly bonding a biologically-active enzyme to dialdehyde cellulose.

Yet another object of this invention is to provide a method for covalently bonding an active enzyme, to dialdehyde cellulose without subjecting the protein to severe reaction conditions.

Still other objects of this invention will readily present themselves to the skilled artisan upon reference to the ensuing specification and the claims.

SUMMARY OF THE INVENTION

The present invention contemplates a water-insoluble, biologically-active conjugate which comprises dialdehyde cellulose and an enzyme covalently bonded directly to said cellulose through a carbon-nitrogen bond.

The biologically-active conjugates of this invention are prepared by reacting dialdehyde cellulose, preferably in fibrous form, with an enzyme through a primary amino group of the enzyme not essential for biological activity. The reaction is carried out in an aqueous medium and at a substantially neutral or alkaline, pH, i.e., at a pH of about 7 or higher.

DESCRIPTION OF THE PREFERRED EMBODIMENTS

For the purposes of the present invention a suitable liquid permeable matrix or carrier for the enzyme is cellulose or water-insoluble derivatives thereof such as methylcellulose, carboxymethyl cellulose, regenerated cellulose, and the like, at least some glucoside units of which have been oxidized to dialdehyde groups and which is substantially neutral, i.e., which is substantially free from carboxyl groups. The term "cellulose" as used herein and in the appended claims is taken to mean cellulose itself and the water-insoluble derivatives thereof.

The degree of oxidation of the cellulose to provide dialdehyde groups can vary. Normally about 5 percent to about 80 percent of the glucoside units in the cellulose polymer are opened and oxidized to dialdehyde groups. A degree of oxidation higher than about 80 percent is undesirable because the structural integrity of the dialdehyde cellulose matrix appears to be impaired. For the purposes of the present invention preferably about 10 percent to about 50 percent of the glucoside units or rings are opened and oxidized to dialdehydes.

Dialdehyde cellulose suitable for the purposes of the present invention can be prepared by the well-known oxidation of cellulose with periodic acid. The oxidation reaction proceeds as follows:

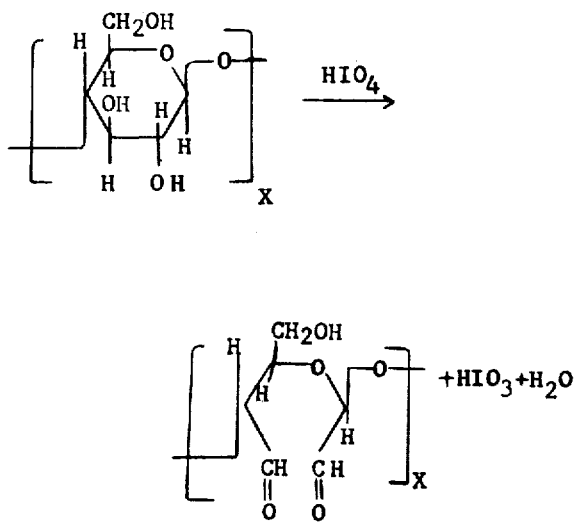

wherein $X$ stands for the number of repeating units in the molecule which may range from about 1000 to about 100,000.

The dialdehyde cellulose can assume a wide variety of physical forms. Dialdehyde cellulose may be in loose fiber form, as fibers woven into a cloth, in porous or sponge form, in granular form, or as a surface coating on an inert material such as amino silylated glass, polyamide fibers, and the like.

Covalent bonding of the enzyme to dialdehyde cellulose occurs through an amino group of the enzyme which is not essential for biological activity. That is, wherein $X$ has the same meaning as before.

A Schiff's Base type aldehyde-primary amine reaction is believed to take place, forming a carbon-to-nitrogen double bond linkage ($>C = N$ —) which can be subsequently reduced to a carbon nitrogen linkage ($>$—C—N$<$), if desired, by catalytic hydrogenation or using an alkali metal borohydride such as sodium borohydride, lithium borohydride, and the like, so as to make the carbon-to-nitrogen bond more stable in acidic media. The bonding reaction can be carried out in an inert or alkaline aqueous medium. Mixed solvent system such as a water-dimethylsulfoxide medium can also be advantageously employed. Temperature and pH of the reaction media are selected so that the biological activity of the enzyme in its intended end use is not adversely affected. For example, temperatures above about 60°C should generally be avoided so as not to cause denaturation of the enzyme. The temperature of choice depends on the particular enzyme or enzymes employed. In general, the reaction temperature can range from about −5°C to about 30°C, and a temperature in the range of about 0°C to about 10°C is preferred.

A wide variety of enzymes can be coupled directly to the dialdehyde cotton carrier. Active enzymes suitable for coupling may be obtained from any suitable source, either vegetable, animal, or microbial. Many such enzymes are available commercially. Typical are the proteolytic enzymes such as the proteases, e.g., neutral and/or alkaline protease. In some instances another differently active enzyme such as amylase can be employed, along or admixed with proteases so as to maximize the operative enzyme activity of the composite. Still other enzymes such as a lipase may be used instead of or in addition to amylase. Other suitable enzymes are esterase, nuclease, or other types of hydrolase. A hydrase or oxidoreductase may also be utilized, depending upon the ultimate activity and intended application.

Many such enzymes can conveniently be obtained from micro-organisms which include bacteria, yeasts, fungi, and the like, by using well-known fermentation methods such as those generally described in KIRK-OTHMER, Encyclopedia of Chemical Technology 8, 173-204. A great many microbially-produced enzymes are available commercially.

The exact activity of the enzyme or enzymes employed as starting material depends on the exact method of preparation and is not critical to the present invention provided only that the enzymatically-active conjugate produced therefrom has the desired enzymatic activity. Various analytical methods are available

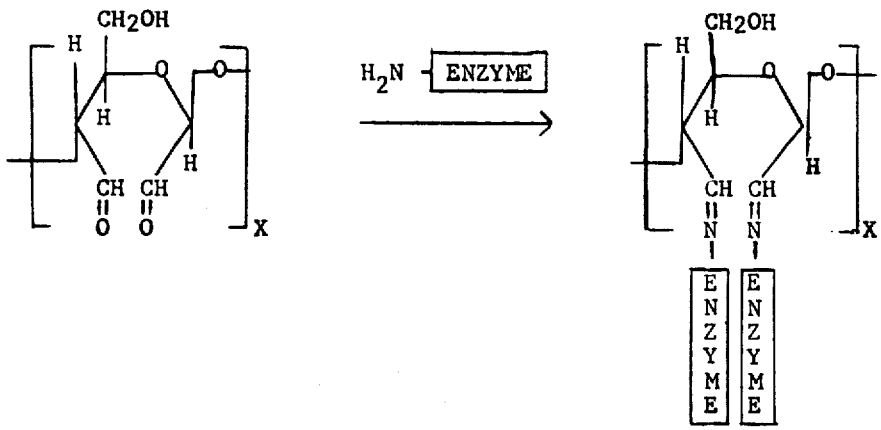

to determine the activity of an enzymatically active material. For example, the protease activity of proteolytic enzymes can be determined by the well-known casein digestion methods. According to such tests, a protease catalyzes the hydrolysis of casein for a certain period of time and temperature, and at a certain pH; the reaction is then stopped by the addition of trichloroacetic acid, and the solution is filtered. The color of the filtrate is then developed by Folin phenol reagent, and the level of enzyme activity is measured spectrophotometrically in units of casein tyrosine. This particular method is more fully described in the Journal of General Physiology 30, 291 (1947) and in Methods of Enzymology 2, 33, Academic Press, New York (1955.) Amylase activity is generally determined by the well-known dinitrosalicylic acid method of Bernfeld. Still other test procedures are known in the art and some are set forth hereinafter.

A particularly effective source of mixed enzymes is a mutated *Bacillus subtilis* organism. The process for producing this organism and enzymes therefrom is described in U.S. Pat. No. 3,031,380. A culture of this *B. subtilis* (Strain AM) organism has been deposited with the United States Department of Agriculture, Agricultural Research Service, Northern Utilization Research and Development Division, 1815 North University Street, Peoria, Ill. 61604, and has been assigned No. NRRL B-3411. The enzymatically active material produced by this organism has been found generally to consist of two proteases, approximately 65 – 75% neutral protease (activity at a pH of 7.0 – 7.5) and about 25–35% alkaline protease (activity at a pH of 9 to 10). A significant amount of amylase is also present. There are generally about $0.7 \times 10^6$ to about $1.2 \times 10^6$ units of neutral protease activity per gram of isolated solids and about $2.5 \times 10^5$ to $4 \times 10^5$ units of alkaline protease activity per gram as determined by Anson's Variation of the Kunitz "Casein" method. There are generally about $3 \times 10^5$ to $3.5 \times 10^5$ units of amylase activity per gram as determined by the Bernfeld method. As pointed out in the cited patent, the relative proportions of protease to amylase will vary depending on the exact conditions of growth of the microorganism, but it has been found that the neutral and alkaline protease and the amylase will be produced, in at least some amounts, almost regardless of changes in the culture medium and other conditions of growth of the microorganism.

Another source of mixed enzymes is *B. subtilis* Strain NRRL 644, *B. subtilis* Strain NRRL 941, and *B. subtilis* Strain IAM 1523 (Japanese Culture Collection). Still other *B. subtilis* microorganisms are available which produce protease, a mixture of proteases, or protease and amylase, at least to a limited if not optimum extent. The so-called *Streptomyces griseus* neutral protease has a broad pH activity range and may constitute one starting enzyme for incorporation into the conjugates of this invention.

Other typical enzymes are trypsin, chymotrypsin, invertase, alkaline phosphatase, urease, ribonuclease, dehydrogenase, and the like.

Examples of application for continuous enzyme reactors having fibrous dialdehyde cotton core and an enzyme covalently bonded thereto are a papain-dialdehyde cotton reactor useful for the chillproofing of beer, a rennin- or pepsin-dialdehyde cotton reactor useful for curdling milk, an amylase-dialdehyde cotton reactor useful for making glucose from starch, a naringinase- or hesperidinase-dialdehyde cotton reactor for the removal of bitter flavors from citrus juices, and the like. Similarly, excess hydrogen peroxide used as a bactericide in milk treatment can be removed therefrom by passing the treated milk through a catalase-dialdehyde cotton reactor. Also, a lactase-dialdehyde cotton reactor can be used to hydrolyze lactose to galactose and glucose.

Enzymes can also be covalently bound to dialdehyde cotton to provide means for clinical analysis and assays, e.g., urease covalently bonded to dialdehyde cotton can be used for blood urea nitrogen determinations, also to provide means for resolving dl-amino acids, e.g., a racemic mixture of N-acylamino acid can be passed through amino acylase-dialdehyde cotton reactor to hydrolyze the l-form thereof which can then be spearated from the d-form.

This invention provides a biologically-active, flow-through reactor wherein an enzyme-containing, liquid-permeable fibrous cellulose is situated in a liquid-permeable reactor which comprises the steps of reacting a liquid-permeable fibrous cellulose with a periodic acid solution for a time sufficient to oxidize 5 to 80 percent of the glucose units in the cellulose to units containing dialdehyde groups, substantially freeing the fibrous dialdehyde cellulose of excess periodic acid, and passing a liquid containing an enzyme at a substantially neutral or alkaline pH through the fibrous dialdehyde cellulose to react the enzyme through a primary amino group thereof not essential for biological activity directly with aldehyde groups of the cellulose so as to form a carbon-nitrogen double bond and thereby binding said enzyme to said fibrous cellulose. In the preferred embodiments few material handling steps are required and exposure of reactive dialdehyde cellulose to undesired atmospheric air or other reactants is minimized if not completely eliminated.

According to the preferred aspects of this invention there is provided a method for preparing a biologically active, flow-through reactor containing active enzymes which reactor is ready for use for a variety of purposes. According to this invention, liquid-permeable fibrous cellulose or one of its equivalents, indicated above, can be placed in a reactor core of a suitable flow-through reactor, either immediately or after it is treated with the periodic acid solution to convert glucose units thereof to units containing dialdehyde groups. Suitable precautions are taken to prevent further oxidation by air or further reaction which compete for aldehyde groups. After freeing the fibrous dialdehyde cellulose of excess periodic acid, a liquid containing a selected enzyme at a substantially neutral or alkaline pH is passed through the fibrous dialdehyde cellulose to react the enzyme through a primary amino group thereof not essential for biological activity directly with aldehyde groups of the cellulose so as to form a carbon-nitrogen double bond and thereby binding the enzyme to the firbrous cellulose. In a most preferred embodiment the untreated liquid-permeable, fibrous cellulose is placed in a liquid flow-through reactor to constitute the liquid permeable biological reactor core. The fibrous cellulose core in the flow-through reactor is exposed to a periodic acid solution for a time sufficient to convert from 5 to 80 percent of the glucose to units containing dialdehyde groups. Then the dialdehyde fibrous cellulose in the flow-through reactor is then substantially freed of excess periodic acid. Then a liquid containing the selected enzyme or enzyme mixture at a substantially neutral or alkaline pH is passed through the fibrous dialdehyde cellulose in the flow-through reactor to react the enzyme through a primary amino group thereof not essential for biological activity directly with aldehyde groups of the cellulose so as to form the carbon-nitrogen double bond and thereby binding the enzyme to the fibrous cellulose core. This embodiment permits easiest control against atmospheric air attack of dialdehyde cellulose intermediate.

The present invention is further illustrated by the following examples.

EXAMPLE 1

Oxidation of Cotton with Periodic Acid

Cotton roving (80 grams) cut in about 1 inch long pieces was washed in a 0.1% dodecylphenol-10 mole ethylene oxide adduct, plus 0.1% sodium carbonate solution (2000 ml) for about 5 to 10 minutes by manual stirring. The resulting slurry was then filtered over a Buchner funnel and the cotton fibres recovered.

The recovered cotton fibers were then rinsed five times with 4000-milliliter aliquots of distilled water with intermittent stirring and filtering after each rinse, followed by rinsing three times with 2000-milliliter aliquots of acetone to remove the water, again with intermittent stirring and filtering after each rinse. Ultimately the washed and rinsed cotton was air dried under a hood.

The dried cotton (50 grams) was placed in a 4 liter Erlenmeyer flask and aqueous, about 0.11 M, periodic acid solution (2.5 liters; pH 1.4) added thereto. The flask was then stoppered using a polyethylene-coated stopper which resists oxidation and the outside of the flask was covered with aluminum foil so as to exclude light. Thereafter, the flask was placed on a platform shaker and shaken for about 5 days at 25°C.

The cotton-periodic acid slurry was then filtered on a glass Buchner funnel, washed five times with a 3- or 4-liter aliquots of water with intermittent stirring and with filtering after each wash, rinsed four times with 2-liter aliquots of acetone with intermittent stirring and with filtering after each rinse, and subsequently placed on a piece of aluminum foil and dried in air under a hood.

Yield: 49.5 grams. After drying in vacuo at 55°C the yield was 46.3 grams, i.e., a moisture loss of 6.5 percent was observed. A control sample (10 grams) after drying in vacuo at 55°C exhibited a moisture loss of 6.0 percent.

A 0.096 N sodium arsenite solution, standardized by 0.104 M potassium permanganate solution, was prepared and used to titrate aliquots of the periodic acid solution before and after cotton oxidation. From the titer data it was calculated that about 57.8 atoms of oxygen per 100 glucoside units had been consumed, that is, about 57.8 percent of glucoside rings in the cotton were opened and oxidized to dialdehydes.

The dialdehyde cotton prepared in the foregoing manner gave a strong blue color when added to an aqueous solution comprising 0.4 M sodium carbonate (5 milliliters) and diluted (3:1) Folin Reagent (1 milliliter), thereby giving a positive test for the presence of reducing, i.e., aldehyde, groups.

EXAMPLE 2

Attachment of Papain to Dialdehyde Cotton

A portion of fibrous dialdehyde cotton (2.5 grams) prepared in Example 1, above, was packed in a stainless steel nipple (0.75 inch I.D. by 1.5 inches long). Foamed polyethylene discs were placed at each end of the packed nipple to retain the fibers and the nipple was closed at both ends with stainless steel caps provided with 1/16-inch inlet and outlet fittings, respectively.

Papain (0.5 grams; purified) was dissolved in water (50 milliliters) and the resulting solution adjusted to pH 8.0 with aqueous 0.2 N sodium hydroxide solution (1.6 milliliters). The papain solution was then recirculated through the prepared dialdehyde cotton reactor bed at a rate of 130 milliliters per minute for 50 minutes and until pH was stable at 8.0. During recirculation 2.0 milliliters of the 0.2 N sodium hydroxide solution were added to the recirculating papain solution to maintain pH at 8.0.

Recirculation of the papain solution was then terminated and the reactor bed washed by pumping therethrough at 130 milliliters per minute two liters of water followed by 2 liters of aqueous 1 M sodium chloride solution.

EXAMPLE 3:

Evaluation of Papain Activity in Reactor

A substrate solution was prepared as follows:

| | |
|---|---|
| 1 | M KCl |
| 0.05 | M KH$_2$PO$_4$ |
| 0.003 | M Disodium salt of ethylene diamine tetraacetic acid (EDTA) |
| 0.003 | M cystein.HCl |
| 0.001 | M benzoyl-L-arginine ethyl ester (BAEE) |

The substrate was then adjusted to pH 6.2 by dilute aqueous sodium hydroxide solution and pumped through the packed papain-dialdehyde cotton reactor prepared in Example 2, above. Hydrolysis of the substrate was monitored by measuring absorbance of the substrate effluent at 253 nm. The test results are compiled in Table I, below.

TABLE I

| Sample No. | Operating Time from Start, min. | Flow Rate ml/min. | Percent Hydrolysis of Effluent |
|---|---|---|---|
| 1 | 16 | 12 | 95 |
| 2 | 25 | 12 | 96 |
| 3 | 30 | 12 | 97 |
| 4 | 35 | 12 | 98 |
| 5 | 40 | 12 | 99 |
| 6 | 50 | 32 | 79 |
| 7 | 60 | 32 | 82 |
| 8 | 68 | 32 | 83 |
| 9 | 82 | 32 | 84 |
| 10 | 86 | 32 | 85 |
| 11 | 102 | 32 | 88 |
| 12 | 105 | 32 | 88 |
| 13 | 110 | 32 | 88 |
| 14 | 117 | 32 | 88 | from the foregoing data it is readily apparent that the papain-dialdehyde cotton reactor gave excellent performance. No leaching of papain from the reactor was noted during the above tests.

After conducting the foregoing tests the papain-dialdehyde cotton reactor core was removed from the reactor, and the fibers washed, with intermittent stirring, 4 times with a 400-milliliter aliquot of water and then 3 times with a 400-milliliter aliquot of acetone. After each wash the fibers were filtered with a glass Buchner funnel without using filter paper. The washed fibers were dried in air and under vacuum at 55°C. The dried fibers had a slight yellow color. A sample of the dried fibers was analyzed for nitrogen. An average nitrogen content of 1.21 percent by weight was found, indicating that 81.5 milligrams of papain were present per gram of dialdehyde cotton.

EXAMPLE 4:

Attachment of Subtilisin to Dialdehyde Cotton

A portion of fibrous dialdehyde cotton (2.5 grams) prepared in Example 1, above, was wetted with water (9 milliliters) and stuffed into a stainless steel pipe (0.625 inch I.D. by 1.5 inches long). Foamed polyethylene discs were placed at each end of the pipe to retain the fibers, and the pipe was capped at both ends with stainless steel caps provided with 1/16-inch inlet and outlet fittings respectively.

Subtilisin (0.400 grams) from B. subtilis and having an activity of $4.1 \times 10^6 \mu/g$ at pH 10 (casein assay) and calcium acetate (0.025 gram) were dissolved in water (41 milliliters) and the solution was stirred while pH was adjusted to 8.0 by the addition of an aqueous solution of 0.2 N sodium hydroxide (1.2 milliliters).

The subtilisin solution was then recirculated through the prepared dialdehyde cotton reactor bed at a rate of 50 milliliters per minute for 1 hour. During recirculation, pH of the solution was maintained at 8.0 by the addition of aqueous 0.2 N sodium hydroxide solution (2 milliliters).

The amount of subtilisin reacted with the dialdehyde cotton was ascertained by comparing the absorbance of the subtilisin solution at 280 nm. before and after recirculation through the dialdehyde cotton. It was found that 52 milligrams of subtilisin had reacted with one gram of dialdehyde cotton.

After recirculation of the subtilisin solution through the reactor bed was completed, the reactor bed was washed by pumping therethrough, at a rate of about 130 milliliters per minute, 2 liters of water, 2 liters of aqueous 1N sodium chloride solution, and two liters of aqueous 0.01 weight percent calcium acetate solution.

EXAMPLE 5:

Evaluation of Subtilisin Activity in Reactor

A substrate solution was prepared by dissolving monobasic potassium phosphate (13.6 grams) in water and making up the volume to 3 liters by adding more water. The pH of the resulting solution was then adjusted to 6.2 by adding aqueous 1N sodium hydroxide solution to the solution. Thereafter benzoyl-L-arginine ethyl ester (1.37 grams) was dissolved in the phosphate solution and the volume thereof made up to four liters by the addition of more water. Final concentrations: 0.05M phosphate and 0.001M benzoyl-L-arginine ethyl ester.

The substrate solution was then pumped through the subtilisin reactor prepared in Example 4, above, at 3.5 ml/min. and the hydrolysis rate of the effluent therefrom monitored by measuring absorbance of the effluent in a flow cell at 253 nm. The obtained data are compiled in Table II below.

TABLE II

| Time from Start, min. | Percent Hydrolysis in Effluent |
|---|---|
| 0 | 0 |
| 13 | 34 |
| 36 | 32 |

TABLE II-continued

| Time from Start, min. | Percent Hydrolysis in Effluent |
|---|---|
| 48 | 32 |
| 65* | 43 |
| 77 | 34 |
| 480 | 26 |

*Calcium acetate added to provide 0.01 weight percent concentration in substrate solution.

EXAMPLE 6:

Attachment of Invertase to Dialdehyde Cotton

A portion of fibrous dialdehyde cotton (2.5 grams) prepared in Example 1, above, was placed into a stainless steel pipe (0.625 inch I.D. by 1.5 inches long). Foamed polyethylene discs were placed at each end of the pipe to retain the fibers, and the pipe was capped at both ends with stainless steel caps provided with 1/16-inch inlet and outlet fittings, respectively.

Invertase (0.500 grams; purified; derived from Baker's yeast, mellibiose free) was dissolved in water (40 milliliters) and pH of the resulting solution was adjusted to 8.0 by the addition of aqueous 0.1 N sodium hydroxide solution (0.4 milliliters).

The thus-prepared invertase solution was then recirculated through the prepared dialdehyde cotton reactor bed at a rate of about 5 to 10 milliliters per minute for 1 hour. During recirculation pH of the solution was maintained at 8.0 by the addition of aqueous 0.1 N sodium hydroxide solution (2 milliliters).

After recirculation of the invertase solution through the reactor bed was completed, the reactor bed was washed by pumping therethrough 1 liter of water, 1 liter of aqueous 1 N sodium chloride solution, one liter of water, and ½ liter of aqueous 1 weight percent sucrose solution in aqueous 0.1 M sodium acetate at a pH of 4.5.

EXAMPLE 7:

Evaluation of Invertase Activity in Reactor

A substrate solution was prepared by dissolving sucrose (1 weight percent) in an aqueous 0.1 M sodium acetate solution at pH 4.5.

The substrate solution at about 25°C was then pumped through the invertase reactor prepared in Example 6, in the obtained effluent mixed with 3,5-dinitrosalicylic acid solution and color developed at 95°C. Hydrolysis was monitored by measuring the absorbance of the effluent admixed with the 3,5-dinitrosalicylic acid solution at 540 nm. The 3,5-dinitrosalicylic acid solution was prepared by dissolving the acid (40 grams) in water (3 liters), adding thereto aqueous 50-weight percent sodium hydroxide solution (128 milliliters), and potassium sodium tartarate (one pound), and then adding sufficient water to make 1 gallon of reagent solution. The experimental data are compiled in Table III, below.

TABLE III

| Time from Start min. | Flow Rate, ml/min. | Percent Hydrolysis of Effluent |
|---|---|---|
| 13 | 5 | 4.0 |
| 18 | 1 | 37.0 |
| 30 | 1 | 36.0 |
| 42 | 1 | 33.8 |
| 57 | 1 | 33.3 |
| 73 | 1 | 32.4 |

TABLE III-continued

| Time from Start min. | Flow Rate, ml/min. | Percent Hydrolysis of Effluent |
|---|---|---|
| 112 | 1 | 32.8 |

EXAMPLE 8:

Attachment of Alkaline Phosphatase to Dialdehyde Cotton

A portion of fibrous dialdehyde cotton (2.5 grams) prepared in Example 1, above, was wetted with water (9 milliliters) and stuffed into a stainless steel pipe (0.625 I.D. by 1.5 inch long). Foamed polyethylene discs were placed at each end of the pipe to retain the fibers, and the pipe was capped at both ends with stainless steel caps provided with 1/16 inch inlet and outlet fittings, respectively.

Alkaline phosphatase (0.500 grams; calf mucosa) was dissolved in water (41 milliliters) and pH of the resulting solution was adjusted from 5.5 to 8.0 by the addition of aqueous 0.2 N sodium hydroxide solution (1.4 milliliters).

The alkaline phosphatase solution was then recirculated for about 40 minutes through the prepared dialdehyde cotton reactor bed at a rate of about 130 milliliters per minute. pH of the recirculating solution was maintained at 8.0 by the addition of aqueous 0.2 N sodium hydroxide solution. A total of 2.6 milliliters of the sodium hydroxide solution was added.

After recirculation of the alkaline phosphatase solution was completed, the reactor bed was washed with water (500 milliliters) and stored for about 16 hours at 5°C. Thereafter the reactor was washed by pumping therethrough 2 liters of water, 2 liters of aqueous 1N sodium chloride solution, and 2 liters of water.

EXAMPLE 9:

Evaluation of Alkaline Phosphatase Activity in Reactor

An aqueous substrate solution having the following concentration was prepared:
0.001 M p-nitrophenylphosphate
0.05 M magnesium chloride
1.0 M tris(hydroxymethyl)aminomethane.HCl (pH 8)

The substrate solution was then pumped through the alkaline phosphatase-dialdehyde cotton reactor at about room temperature and the reactor effluent monitored for hydrolysis by measuring absorbance at 410 nm. The experimental data are compiled in Table IV, below.

TABLE IV

| Time from Start, min. | Flow Rate ml/min. | Percent Hydrolysis of Effluent |
|---|---|---|
| 0 | 0 | 0 |
| 52 – 56 | 7 | 1.3 |
| 60 | 1.5 | — |
| 83 | 1.5 | 6.4 |
| 102 | 1.5 | 7.0 |
| 390 | 1.5 | 9.8 |
| 408 | 7 | 1.98 |
| 528* | 7 | — |
| 577 | 2 | 4.3 |
| 607 | 2 | 4.25 |
| 646 | 2 | 4.19 |
| 678 | 2 | 4.22 |
| 714 | 2 | 3.95 |

TABLE IV-continued

| Time from Start, min. | Flow Rate ml/min. | Percent Hydrolysis of Effluent |
|---|---|---|
| 723 | 2 | 3.95 |

*Fresh batch of substrate solution prepared and pumped through at this point in time.

EXAMPLE 10:

Attachment of alpha-Amylasee to Dialdehyde Cotton

A portion of fibrous dialdehyde cotton (2.5 grams) prepared in Example 1, above, was wetted with water (9 milliliters) and packed into a stainless steel pipe (0.75 inch I.D. by 1.5 inches long). Foamed polyethylene discs were placed at each end of the pipe to retain the fibers, and the pipe was capped at both ends with stainless steel caps provided with 1/16-inch inlet and outlet fittings, respectively.

alpha-Amylase (0.400 grams; 4 times recrystallized; derived from B. subtilis) and
calcium acetate (0.025 gram) were dissolved in 41 milliliters of water and 0.1 N aqueous sodium hydroxide solution (1.0 milliliters) was added to the resulting solution in order to adjust the pH thereof to 8.0.

The alpha-amylase solution was then recirculated for about 40 minutes through the prepared dialdehyde cotton reactor bed at a rate of about 130 milliliters per minute. The recirculating solution was maintained at a pH of 8.0 by the addition of 2.1 milliliters of 1 N aqueous sodium hydroxide solution.

After recirculation of the alpha-amylase solution was terminated, the reactor bed was washed by pumping therethrough, at a rate of 130 milliliters per minute, 2 liters of water, 2 liters of 1 M aqueous sodium chloride solution, and 2 liters of water.

EXAMPLE 11:

Evaluation of alpha-Amylase Activity in Reactor

An aqueous substrate solution was prepared by slurrying soluble starch (20 grams) in a beaker of cold water (100 milliliters) and then stirring the slurry into boiling water (1000 milliliters). Any starch remaining in the beaker was washed into the boiling water using 3 to 50 milliliters of cold water.

Boiling was continued for two minutes, the resulting solution cooled, and a 0.05 M aqueous sodium acetate buffer solution (200 milliliters; pH 6.0) added to adjust the pH to 6.0 and to bring the volume up to 2 liters. The thus-produced substrate solution was then stored for about 16 hours at about 0°C. to 5°C. and calcium acetate (1.00 grams) was added thereto to give 0.05 weight percent acetate, i.e., 11.1 mg/ml glucose equivalent, in the resulting solution.

A reagent for the detection of reducing groups (DNS Reagent) was prepared by dissolving 3,5-dinitrosalicylic acid (40 grams) in water (3 liters), adding thereto aqueous 50-weight percent sodium hydroxide solution (128 milliliters), and potassium sodium tartarate (1 lb.), adding sufficient water to make 1 gallon of reagent solution.

The prepared substrate solution was then pumped through the alpha-amylase-containing reactor of Example 10, above, at about room temperature and the degree of starch hydrolysis in the reactor noted by mixing a portion of the reactor effluent (0.36 milliliters per minute) with the DNS Reagent (2.63 milliliters per minute), heating the mixture to 95°C for about 10 minutes to develop color, cooling the mixture, and measuring the absorbance of the resulting solution at 540 nm. The experimental data are compiled in Table V, below.

TABLE V

| Time from Start, min. | Flow Rate, ml/min. | Contact Time, sec. | Percent Hydrolysis of Effluent | Mg. of Reducible Sugar per ml. of Effluent |
|---|---|---|---|---|
| 15 | 3 | 160 | >30 | >3.3 |
| 30 | 10 | 48 | ca. 22 | 2.44 |
| 55 | 30 | 16 | 13.5 | 1.5 |

EXAMPLE 12:

Attachment of alpha-Amylase to Dialdehyde Cotton

A portion of fibrous dialdehyde cotton (2.5 grams) prepared in Example 1, above, was wetted with water (9 milliliters) and packed into a stainless steel pipe (0.75 inch I.D. by 1.5 inches long). Foamed polyethylene discs were placed at each end of the pipe to retain the fibers, and the pipe was capped at both ends with stainless steel caps provided with 1/16-inch inlet and outlet fittings, respectively.

alpha-Amylase (0.400 grams; 4 times recrystallized; derived from B. subtilis) was dissolved in 41 milliliters of water and 0.1 N aqueous sodium hydroxide solution (0.7 milliliters) was added to the resulting solution in order to adjust the pH thereof to 8.0.

The alpha-amylase solution was then recirculated for about 35 minutes through the prepared dialdehyde cotton reactor bed at a rate of about 130 milliliters per minute. The recirculating solution was maintained at a pH of 8.0 by the addition of 1.7 milliliters of 1 N aqueous sodium hydroxide solution.

After recirculation of the alpha-amylase solution was terminated the reactor bed was washed by pumping therethrough, at a rate of 130 milliliters per minute, 2 liters of water, 2 liters of 1M aqueous sodium chloride solution, and 2 liters of water.

EXAMPLE 13:

Evaluation of alpha-Amylase Activity

An aliquot of the aqueous substrate solution prepared in Example 11 was pumped through the reactor of Example 12 at room temperature and at a rate of 30 milliliters per minute for 25 minutes. The degree of starch hydrolysis was determined in the same manner as set forth in Example 11. In the reactor effluent about 7.0 percent of hydrolyzed starch was noted.

EXAMPLE 14:

Chillproofing of Beer in a Dialdehyde Cotton Reactor

A cartridge comprising cotton yarn was wound to a depth of 0.75 inch on a roll made of stainless steel screen (1 O.D. by 4 inches long). Outside dimensions of the cartridge were 2.5 diameter by 4 inches long.

The cartridge was placed in a stainless steel holder and 3.5 liters of aqueous 0.11 M periodic acid solution was recirculated through the cartridge for 4 days. Thereafter the cartridge was washed with 30 liters of water and a papain solution (16 grams papain in 1000 milliliters of water; pH 8.0) was recycled through the periodic acid-treated cartridge. Then the excess papain was washed out with water, 1 M aqueous sodium chloride solution, and more water.

For the treatment of beer the prepared cartridge was first conditioned by recycling therethrough draft beer containing about 0.2 to about 0.3 weight percent protein, i.e., not chillproofed, for 24 hours at 5°C. an at a rate of 1 liter per minute. Thereafter 5 kilograms of test beer (not chillproofed) was recycled through the cartridge at 5°C. for 4 days at a rate of 1 liter per minute. Pressure drop across the cartridge was observed to be 2.25 psig. In another test run, beer was passed through the prepared cartridge at 5°C. in a single pass at a rate of 400 milliliters per minute. The beer was bottled and stored as indicated in Table VI, below.

The treated beer effluent from the cartridge was tested for the presence of papain with Azocoll (Bremer et al., Am. Assoc. of Brewing Chemists, 1967, 236).

The experimental data are compiled in Table VI, below.

TABLE VI

BEER TEST DATA

| Run No. | Treatment of Beer Before Bottling | Hazemeter Readings/Days at 40°C* | | | | | | | | Presence of Papain in Treated Beer by Azocoll |
|---|---|---|---|---|---|---|---|---|---|---|
| | | 1 | 2 | 4 | 9 | 14 | 21 | 27 | 37 | |
| 1A | Control - None | 645 | | | | | | | | 0 |
| 1B | (No treatment) | 660 | | | | | | | | |
| 1C | | 655 | | | | | | | | |
| 2A | Papain-DIALC** — One pass at 400 ml/min. | 445 | | | | | | | | 0 |
| 2B | | 475 | | | | | | | | |
| 2C | (20 seconds contact) | 435 | | | | | | | | |
| 3A | Papain-DIALC** — 4 days at 1L/min. | 43 | 42 | 42 | 42 | 48 | 52 | 56 | 66 | 0 |
| 3B | (>1100 passes; 0.4 day total | 37 | 38 | 41 | 45 | 47 | 52 | 56 | 66 | |
| 3C | contact) | 38 | 39 | 38 | 43 | 47 | 54 | 56 | 72 | |
| 4A | Soluble Papain at 20 mg/L | 180 | 202 | 280 | | | | | | ++++ |
| 4B | (Free Papain dissolved in beer) | 181 | 202 | 292 | | | | | | |
| 4C | | 178 | 200 | 245 | | | | | | |

*Beer chilled 24 hrs. at 0°C; after storage at 40°C; and then read on hazemeter. Following this it is returned to 40°C. and recycled, etc. >250 haze not acceptable.
**Dialdehyde Cotton.

From the above data it is readily apparent that an extremely effective reactor for chillproofing beer can be prepared by covalently bonding papain to dialdehyde cotton in accordance with the teachings of the present invention.

The foregoing discussion and the Examples are intended as illustrative and are not to be construed as limiting. Still other variations within the spirit and scope of the present invention will readily present themselves to one skilled in the art.

We claim:

1. A method for producing a biologically active flow-through reactor which comprises the steps of
    reacting a liquid permeable fibrous cotton with a periodic acid solution for a time sufficient to oxidize 5 to 80 percent of the glucose units in the cotton to units containing dialdehyde groups;
    substantially freeing the fibrous dialdehyde cotton of excess periodic acid;
    placing the fibrous dialdehyde cotton in a liquid permeable, flow-through reactor to constitute an elongated reactor core, and
    passing a liquid containing an enzyme at a substantially neutral or alkaline pH through the fibrous dialdehyde cotton in the liquid permeable, flow-through reactor to react the enzyme through a primary amino group thereof not essential for biological activity directly with aldehyde groups of the cotton so as to form a carbonnitrogen double bond and thereby binding said enzyme to said core.

2. Method in accordance with claim 1 wherein the enzyme is papain.

3. A method for producing a flow-through reactor which comprises providing a liquid permeable biological reactor core containing an elongated liquid permeable mass of fibrous cotton in a flowthrough reactor;
    exposing the liquid permeable fibrous cotton in the flow-through reactor to a periodic acid solution for a time sufficient to convert from 5 to 80 percent of the glucose units in the cotton to dialdehyde groups;
    substantially freeing the dialdehyde fibrous cotton in the flow-through reactor of excess periodic acid, and
    passing a liquid containing an enzyme at a substantially neutral or alkaline pH through the fibrous dialdehyde cotton in the flow-through reactor to react the enzyme through a primary amino group thereof not essential for biological activity directly with aldehyde groups of the cotton so as to form a carbon-nitrogen double bond and thereby binding said enzyme to said core.

4. Method of claim 3 which further includes the step of passing a liquid containing a substrate for said enzyme through the reactor.

5. Method of claim 4 wherein the substrate containing liquid is beer.

6. Method in accordance with claim 3 wherein the enzyme is papain.

7. The method in accordance with claim 3 wherein the enzyme is alpha-amylase.

8. The method in accordance with claim 3 wherein the enzyme is subtilisin.

* * * * *